US006218544B1

(12) United States Patent
Li et al.

(10) Patent No.: US 6,218,544 B1
(45) Date of Patent: Apr. 17, 2001

(54) HETEROCYCLIC ESTERS AND AMIDES

(75) Inventors: Jia-He Li, Cockeysville; Gregory S. Hamilton, Catonsville, both of MD (US)

(73) Assignee: Gpi Nil Holdings, Inc., Wilmington, DE (US)

( * ) Notice: Subject to any disclaimer, the term of this patent is extended or adjusted under 35 U.S.C. 154(b) by 0 days.

(21) Appl. No.: 09/442,628

(22) Filed: Nov. 18, 1999

Related U.S. Application Data

(62) Division of application No. 09/027,622, filed on Feb. 23, 1998, which is a division of application No. 08/719,947, filed on Sep. 25, 1996, now Pat. No. 5,801,187.

(51) Int. Cl.$^7$ .................................................. C07D 277/06
(52) U.S. Cl. ............................................................. 548/201
(58) Field of Search ................................................ 548/201

(56) References Cited

U.S. PATENT DOCUMENTS

| | | | |
|---|---|---|---|
| 3,385,918 | 5/1968 | Connell et al. | 260/180 |
| 4,310,461 | 1/1982 | Krapcho et al. | 546/188 |
| 4,390,695 | 6/1983 | Krapcho et al. | 546/216 |
| 4,531,964 | 7/1985 | Shimano et al. | 260/326.2 |
| 4,578,474 | 3/1986 | Krapcho et al. | 71/92 |
| 4,593,102 | 6/1986 | Shanklin, Jr. | 544/130 |
| 4,808,573 | 2/1989 | Gold et al. | 514/19 |
| 4,818,749 | 4/1989 | Gold et al. | 514/19 |
| 5,192,773 | 3/1993 | Armistead et al. | 514/330 |
| 5,252,579 | 10/1993 | Skotnicki et al. | 514/291 |
| 5,294,603 | 3/1994 | Rinehart et al. | 514/10 |
| 5,330,993 | 7/1994 | Armistead et al. | 514/330 |
| 5,347,042 | 9/1994 | Grosse-Bley et al. | 560/153 |
| 5,359,138 | 10/1994 | Takeuchi et al. | 562/567 |
| 5,414,083 | 5/1995 | Hackl et al. | 544/19 |
| 5,447,915 | 9/1995 | Schreiber et al. | 514/18 |
| 5,614,547 | 3/1997 | Hamilton et al. | 514/423 |
| 5,696,135 | 12/1997 | Steiner et al. | 514/317 |
| 5,721,256 | 2/1998 | Hamilton et al. | 514/330 |
| 5,786,378 | 7/1998 | Hamilton et al. | 514/423 |
| 5,795,908 | 8/1998 | Hamilton et al. | 514/423 |
| 5,798,355 | 8/1998 | Steiner et al. | 514/248 |
| 5,801,187 | 9/1998 | Li et al. | 514/365 |
| 5,801,197 | 9/1998 | Steiner et al. | 514/548 |
| 6,037,370 | 3/2000 | Armistead | 514/533 |

FOREIGN PATENT DOCUMENTS

| | | |
|---|---|---|
| 3508251 | 9/1986 | (DE) . |
| 3931051 | 3/1990 | (DE) . |
| 4015255 | 11/1991 | (DE) . |
| 4120695 | 12/1992 | (DE) . |
| 12401 | 6/1980 | (EP) . |
| 38117 | 10/1981 | (EP) . |
| 48159 | 3/1982 | (EP) . |
| 50800 | 5/1982 | (EP) . |
| 73143 | 3/1983 | (EP) . |
| 88350 | 9/1983 | (EP) . |
| 196841 | 10/1986 | (EP) . |
| 260118 | 3/1988 | (EP) . |
| 333174 | 9/1989 | (EP) . |
| 352000 | 1/1990 | (EP) . |
| 378318 | 7/1990 | (EP) . |
| 405994 | 1/1991 | (EP) . |
| 419049 | 3/1991 | (EP) . |
| 468339 | 1/1992 | (EP) . |
| 564924 | 3/1993 | (EP) . |
| 572365 | 12/1993 | (EP) . |
| 652229 | 5/1995 | (EP) . |
| 2247456 | 3/1992 | (GB) . |
| 04149166 | 5/1992 | (JP) . |
| 05178824 | 7/1993 | (JP) . |
| WO 8809789 | 12/1988 | (WO) . |
| WO 9012805 | 11/1990 | (WO) . |
| WO 9104985 | 4/1991 | (WO) . |
| WO 9113088 | 9/1991 | (WO) . |
| WO 9200278 | 1/1992 | (WO) . |
| WO 9203472 | 3/1992 | (WO) . |
| WO 9216501 | 10/1992 | (WO) . |
| WO 9218478 | 10/1992 | (WO) . |
| WO 9219593 | 11/1992 | (WO) . |
| WO 9736869 | 11/1992 | (WO) . |
| WO 9221313 | 12/1992 | (WO) . |
| WO 9313066 | 7/1993 | (WO) . |
| WO 9325546 | 12/1993 | (WO) . |
| WO 9405639 | 3/1994 | (WO) . |
| WO 9407858 | 4/1994 | (WO) . |
| WO 9413629 | 6/1994 | (WO) . |
| WO 9512572 | 5/1995 | (WO) . |
| WO 9535308 | 12/1995 | (WO) . |
| WO 9606097 | 2/1996 | (WO) . |
| WO 9615101 | 5/1996 | (WO) . |
| WO 9617816 | 6/1996 | (WO) . |
| 9207782 | 4/1983 | (ZA) . |

OTHER PUBLICATIONS

Dunkerton et al., Chemical Abstract 94:84059, 1981.*

Vasella, A. et al., "Synthesis of D– and L–5–Oxaproline and of a New Captopril Analogue," *Helvetica Chimica Acta*, 1983, 66(4), 1241–1252.

Dunkerton, Lois V. et al., "Synthetic Approaches to Bicyclomycin I. Preparation of Monocyclic Intermediates by Retrograde Michael Cleavage of 6–Alkyl–6–Methoxyhexahydro–3H–Thiazclo [3,4–a]Pyrazine–5,8–Diones," *Tetrahedron Lett.*, 1980, 21(19), 1803–1806.

Askin, D. et al., "Efficient degradation of FK–506 to a versatile synthetic intermediate," *J. Org. Chem.*, 1990, 55(20), 5451–4.

(List continued on next page.)

Primary Examiner—Mukund J. Shah
Assistant Examiner—Deepak R. Rao
(74) Attorney, Agent, or Firm—Gary M. Nath; Todd L. Juneau; Joshua B. Goldberg

(57) ABSTRACT

This invention relates to neurotrophic low molecular weight, small molecule heterocyclic esters and amides having an affinity for FKBP-type immunophilins, and their use as inhibitors of the enzyme activity associated with immunophilin proteins, particularly peptidyl-prolyl isomerase, or rotamase, enzyme activity.

1 Claim, 2 Drawing Sheets

OTHER PUBLICATIONS

Goulet, Mark T., and Boger, Joshua, "Degrative studies on the tricarbonyl containing macrolide rapamycin", *Tetrahedron Lett.*, 1990, 31(34), 4845–8.

Jones, T. et al., "Chemistry of tricarbonyl hemiketals and application of Evans technology to the total synthesis of the immunosuppressant (–)–FK–506", *J. Am. Chem. Soc.*, 1990, 112(8), 2998–3017.

Jones, A. et al., "A formal synthesis of FK–506. Exploration of some alternatives to macrolactamization", *J. Org. Chem.*, 1990, 55(9), 2786–97.

Rao, A.V., et al., "Studies directed towards the synthesis of immunosuppresive agent FK–506: construction of the tricarbonyl moiety", *Tetrahedron Lett.*, 1990, 31(10), 1439–42.

Harding, M.W., et al., "A recpetor for the immunosuppressant FK506 is a cis–trans peptidyl–prolyl isomerase", *Nature Lett.*, 1989, 341, 758–60.

Finberg, Robert W. et al., "Prevention of HIV–1 Infection and Preservation of CD4 Function by the Binding of CPFs to gp120," *Science*, 1990, 249, 287–91.

Goodfellow, Val S. et al., "p–Nitrophenyl 3–diazopyruvate and diazopyruvamides, a New Family of Photoactivatable Cross–Linking Bioprobes," *Biochemistry*, 28(15), 6346–60.

Wasserman, H.H. et al., "Synthesis of the tricarbonyl region of FK–506 through and amidophosphorane [Erratum to document cited in CA111(7):5766p]", *J. Org. Chem.*, 1989, 54(22), 5406.

Wasserman, H.H. et al., "Synthesis of the tricarbonyl region of FK–506 through an amidosphere", *J. Org. Chem.*, 1989, 54(12), 2785–6.

Askin, D. et al., "Chemistry of FK–506: benzilic acid rearrangement of the tricarbonyl system," *Tetrahedron Lett.*, 1989, 30(6), 671–4.

Coleman, R. and Danishefsky, S. "Degradation and manipulations of the immunosuppressant FK506: preparation of potential synthetic intermediates", *Heterocycles*, 1989, 28(1), 157–61.

Faelth, Lars et al., "Interactions between C=S groups in 1,2– and 1,3–bis(thiocarbonyl) compounds: A study by spectroscopy, x–ray crystallography, and CNDO/S Calculations", *Theochem*, 1989, 55, 239–59.

Boulmedais, Ali et al., "Stereochemistry of Electrochemical Reduction of Optically Active α–ketoamides. II. Electroreduction of benzoylformamides derived from S–(–)–proline," *Bull. Soc. Chim. Fr.*, 1988, (2), 185–91. (French).

Soai, Kenso et al., "Asymmetric Allylation of α–keto amides derived from (S)–proline esters," *Pept. Chem.*, 1986, 24, 327–330.

Munegumi, Toratane et al., "Asymmetric Catalytic Hydrogenations of N–pyruvoyl–(s)–proline esters", *Bull. Chem. Soc. Jpn.*, 1987, 60(1), 243–53.

Egbertson, M. and Danishefksy, S., "A synthetic route to the tricarbonyl region of FK–506", *J. Org. Chem.*, 1989, 54(1), 11–12.

Williams, D.R. and Benbow, J.W., "Synthesis of the α,β diketo amide segment of the novel immunosuppressive FK506", *J. Org. Chem.*, 1988, 53(191), 4643–4.

Kocienski, P. et al., "A synthesis of the C(1)–C(15) segment of tsukubaenolide (FK506)", *Tetrahedron Lett.*, 1988, 29(35), 4481–4.

Tanaka, H, et al., "Structure of FK506, a novel immunosuppressant isolated from Streptomyces," *J. Am. Chem. Soc.*, 1987, 109(16), 5031–3.

Soai, Kenso et al., "Asymmetric Synthesis of Functionalized tertiary alcohols by diastereoselective allylation of chiral α–keto amides derived from (S)–proline esters: control of stereochemistry based on saturated coordination of Lewis acid", *J. Org. Chem.*, 1986, 57(17) 3290–5.

Soai, Kenso et al., "Asymmetric synthesis of both eaniomers of α–hydroxy acids by the diastereoselective reduction of chiral α–keto amides with complex metal hydrides in the presence of a metal salt", *Chem. Lett.*, 1986, 11, 1897–900.

Soai, Kenso et al., "Diastereoselective reduction of chiral α–ketoamides derived from (S)–proline esters with sodium borohydride. Preparation of optically active α–hydroxy acids", *J. Chem. Soc.*, 1985, 1(4), 769–72.

Soai, Kenso et al., "Diastereoselective asymmetric allylation of chiral α–keto amides with allyltrimethylsilane. Preparation of protected homoallylic alcohols", *J. Chem. Soc.*, 1984, 15, 1016–1017.

Soai, Kenso et al., "Sodium borohydride as diastereoselective reducing agent of chiral α–keto amides", *Pept. Chem.*, 1982, 20, 81–4.

Bender, D. et al., "Periodate oxidation of α–keto γ–lactams. Enol oxidation and β–lactam formation. Mechanism of periodate hydroxylation reactions", *J. Org. Chem.*, 1978, 43(17), 3354–62.

Colombo, L. et al., "Enantioselective synthesis of secondary alcohols in the presence of chiral ligands", *Tetrahedron*, 1982, 38(17), 2725–7.

Soai, Kenso et al., "Unusual effect of a mixed solvent in the asymmetric reduction of chiral α–keto amides with sodium borohydride", *J. Chem. Soc.*, 1982, 21, 1282–3.

Steglich, Wolfgang et al., "Activated carboxylic acid derivatives. II. A simple synthesis of 2–oxycarboxylic acid amides, N–(2–oxoacyl)amino acid esters and 2–oxocarboxylic acid hydrazides", *Synthesis*, 1978, 8, 622–4.

Cushman, D.W. et al., "Design of potent competitive inhibitors of angiotensin–converting enzyme. Carboxyalkanoyl and mercaptoalkanoyl amino aicds," *Biochemistry*, 1977, 16(25), 5484–91.

Steglich, Wolfgang and Hinze, Sabine, "A rational synthesis of N–trifluoroacetylamino acids", *Synthesis*, 1976, 8, 399–401.

Bycroft, Barrie W. et al., "Efficient asymmetric synthesis of α–amino from α–keto acids and ammonia with conservation of the chiral reagent", *J. Chem. Soc.*, 1975, 24, 988–9.

Marshall, J.A. et al., "Covenient synthesis of dioxopiperazines via aminolysis of α–(pyruvoylamino) esters", *Synth. Commun.*, 1975, 5(3), 237–44.

Haeusler, Johannes et al., "Amino acids and peptides. IX. Pyruvoyl amino acids", *Chem. Ber.*, 1974, 107(1), 145–51.

Hearn, Walter R. et al., "L–Proline–N–oxalic anhydride", *J. Org. Chem.*, 1967, 32(12) 4072–4.

Chakaraborty, Tushar K., "Studies towards the development of cyclic peptide–based analogs of macrolide immunosuppressants", *Pure Appl. Chem.*, 1996, 68(3) 565–568.

Ponticelli, Claudio, "Treatment of the Nephrotic Syndrome with Cyclosporin A", *J. of Autoimmunity*, 1992, 5, 315–24.

Tindall, Richard S. A., "Immunointervention with Cyclosporin A in autoimmune Neurological Disorders", *J. of Autoimmunity*, 1992, 5, 301–13.

Tugwell, Peter, "Cyclosporin in the Treatment of Rheumatoid Arthritis", *J. of Autoimmunity*, 1992, 5, 231–40.

Fry, Lionel, "Psoriasis: Immunopathology and Long–term treatment with Cyclosporin", *J. of Autoimmunity*, 1992, 5, 277–83.

Feutren, Gilles, "The optimal use of Cyclosporin A in autoimmune diseases," *J. of Autoimmunity*, 1992, 5, 183–95.

Slee, Deborah H. et al., "Selectivity in the inhibition of HIV and FIV protease: Inhibitory and mechanistic studies of pyrrolidine–containing α–keto amide and hydroxyethylamine core structures", *J. Am. Chem. Soc.*, 1995, 117(48), 1187–78.

Nicolaou, K.C. et al., "Total synthesis of rapamycin", *Che.–Eur. J.*, 1995, 1(5), 318–33.

Munoz, Benito et al., "α–Ketoamide Phe–Pro isostere as a new core structure for the inhibition of HIV protease", *Bioorg. Med. Chem.*, 1994, 2(10), 1085–90.

Hauske, James R. et al., "Investigation of the effects if synthetic, non–cytotoxic immunophilin inhibitors on MDR", *Bioorg. Med. Chem. Lett.*, 1994, 4(17), 2097–102.

Mashkowskii, M.D. et al., "1–[4–(2–Hydroxy–3–tert–butyl aminopropoxy)–indole–3–yl (5–acetamido–1–(S)–carboxypentyl)–DL–anayl]–L–proline dihydrochloride, a new angiotensin–converting enzyme inhibitor with β–adrenoblocking properties", *Khim.–Farm. Zh.*, 1993, 27(10), 16–20.

Ranganathan, Darshan et al., "Protein Backbone Modification by Novel Cα–C Side–Chain Scission", 1994, *J. Am. Chem. Soc.*, 116(15), 6545–57.

Baader, Ekkehard et al., "Inhibition of prolyl 4–hydroxylase by oxalyl amino acid derivative in vitro, in isolated microsomes and in embryonic chicken tissues", *Biochem. J.*, 1994, 300(2), 525–30.

Holt, Dennis A. et al., "Structure–activity of synthetic FKBP ligands as peptidyl–prolyl isomerase inhibitors", *Bioorg. Med. Chem. Lett.*, 1994, 4(2), 315–20.

Karle, Isabella L. et al., "Conformation of the oxalamide group in retro–bispeptides. Three crystal structures" *Int. J. Pept. Protein Res.*, 1994, 43(2), 160–5.

Kaczmar et al., *Makromol. Chem.*, 1976, 177, 1981–9.

Steiner, Joseph P. et al., "High brain densities of the immunophilin FKBP colocalized with calcineurin", *Nature Lett.*, 1992, 358, 584–7.

Pattenden, Gerald et al., "Facile Synthesis of the tricarbonyl subunit in the immunosuppressant rapamycin", *Tetrahedron Lett.*, 1993, 34(16), 2677–80.

Furber, M. et al., "Studies relating to the immunosuppressive activity of FK506", *Tetrahedron Lett.*, 1993, 34(8), 1351–4.

Ranganathan, Darshan et al., "Oxalopeptides as core motifs for protein design", *J. Chem. Soc.*, 1993, (1), 92–4.

Dawson, Ted M. et al., "Immunosuprpessant FK506 enhances phosphorylation of nitric oxide synthase and protects against glutamate neurotoxicity", *Proc. Natl. Acad. Sci. USA*, 1993, 90, 9808–12.

Cunliffe, C. Jane et al., "Novel inhibitors of prolyl 4–hydroxylase. 3. Inhibition by the substrate analog N–oxaloglycine and its derivatives", *J. Med. Chem.*, 1992, 35(14), 2652–8.

Waldmann, Herbert, "Amino acid esters as chiral auxiliaries in Barbier–type reactions in aqueous solutions", *Liebigs Ann. Chem.*, 1991, (12), 1317–22.

Krit, N.A. et al., "Impact of the nature of alkyl radical on the biological activity of N–carboxyalkyl dipeptides", *Khim.– Farm. Zh.*, 1991, 25(7), 44–6.

Blaschke et al., Chemical abstracts, 1974, 85, 78405k.

Caufield, Craig E. and Musser, John H., *Annual Reports in Medicinal Chemistry*, Johns (Ed.), Academic Press, Inc., Chapter 21, 195–204, 1989.

Effenberger, F. et al., "Diastereoselective addition of benzenesulfenyl chloride to 1–acryloylproline esters", *Chemical Abstracts*, 1989, 10, 778–9.

Nakatsuta, M. et al., "Total Synthesis of FK506 and an FKBP Reagent, $(C_8, C_9-^{13}C_2)$–FK–506", *J. Am. Chem. Soc.*, 1990, 112(14), 5583–90.

Shu, A. et al., "Synthesis of I–125 labeled photoaffinity rapamycin analogs", *J. Labelled Compd. Radiopharm.*, 1996, 38(3), 277–37.

Tatlock, J. et al., "High affinity FKBP–12 ligands from (R)–(–)–carvone. Synthesis and evaluation of FK506 pyranose ring replacements", *Bioorg. Med. Chem. Lett.*, 1995, 5(21), 2489–94.

Teague, S. et al., "Synthesis of FK506–cyclosporin hybrd macrocycles", *Bioorg. Med. Chem. Lett.*, 1995, 5(20), 2341–6.

Stocks, M. et al., "Macrocyclic ring closures employing the intramolecular Heck reaction", *Tetrahedron Lett.*, 1995, 36(36), 6555–8.

Wang, C.P. et al., "High performance liquid chromatographic isolation and spectroscopic characterization of three major metabolites from the plasma of rats receiving rapamycin (sirolimus) orally", *J. Lig. Chromatogr.*, 1995, 18(13), 2559–68.

Armistead, D.M. et al., "Design, synthesis and structure of non–macrocyclic inhibitors of FKBP12, the major binding protein for the immunosuppressant FK506", *Acta Crystallogr.*, 1995, D51(4), 522–8.

Luengo, J. et al., "Structure–activity studies of rapamycin analogs: evidence that the C–7 methoxy group is part of the effector domain and positioned at the FKBP:12–FRAP interface", *Chem. Biol.*, 1995, 2(7), 471–81.

Furber, Mark, "FKBP–12–ligand–calcineurin interactions: analogs of SBL506", *J. Am. Chem. Soc.*, 1995, 117(27), 7267–8.

Chakraborty, TK et al., "Design and Synthesis of a rapamycin–based high affinity binding FKBP12 ligand", *Chem. Biol.*, 1995, 2(3), 157–61.

Wang, C.P. et al., "A high performance liquid chromatographic method for the determination of rapamycin (sirolimus) in rat serum, plasma, and blood and in monkey serum", *J. Liq. Chromatogr.*, 1995, 18(9), 1801–8.

Smith, A.B. et al., "Total synthesis of rapamycin and demethoxyrapamycin", *J. Am. Chem. Soc.*, 1995, 117(19).

Baumann, K. et al., "Synthesis and oxidative cleavage of the major equilibrium products of ascomycin and FK506", *Tetrahedron Lett.*, 1995, 26(13), 2231–4.

Nelson, F. et al., "A novel ring contraction of rapamycin", *Tetrahedron Lett.*, 1994, 35(41), 7557–60.

Dawson, T.M. et al., "The immunophilins, FK506 binding and cyclophilin are discretely localized in the brain: relationship to calcineurin", *Neuroscience*, 1994, 62(2), 569–80.

Cameron, Andrew et al., "Immunophilin FK506 binding protein associated with inositol 1,4,5–triphosphate receptor modulates calcium flux", *Proc. Natl. Acad. Sci. USA*, 1995, 92, 1784–1788.

Stocks, M. et al., "The contribution to the binding of the pyranoside substituents in the excised binding domain of FK–506", *Bioorg. Med. Chem. Lett.*, 1994, 4(12), 1457–60.

Steiner, J.P. et al., "Nonimmunosuppressive Ligands for Neuroimmunophilins Promote Nerve Extension In Vitro and In Vivo", *Society for Neuroscience Abstracts*, 1996, 22, 297.13.

Lyons, W. Ernest et al., "Neuronal Regeneration Enhances the Expression of the Immunophilin FKBP–12", *The Journal of Neuroscience,* 1995, 15, 2985–94.

Skotnicki, Jerauld et al., "Ring expanded rapamycin derivatives", *Tetrahedron Lett.,* 1994, 35(2), 201–2.

Skotnicki, Jerauld et al., "Synthesis of secorapamycin esters and amides", *Tetrahedron Lett.,* 1994, 35(2), 197–200.

Rao, A.V. Rama et al., "Studies directed towards the synthesis of rapamycin: stereoselective synthesis of C–1 to C–15 segment", *Tetrahedron Lett.,* 1993, 34(44), 7111–14.

Andrus, Merrit B., "Structure–based design of an acyclic ligand that bridges FKBP12 and calcineurin", *J. Am. Chem. Soc.,* 1993, 115(2), 10420–1.

Luengo, Juan I. et al., "Efficient removal of pipecolinate from rapamycin and FK506 by reaction with tetrabutylammonium cyanide", *Tetrahedron Lett.,* 1993, 34(29), 4599–602.

Steffan, Robert J. et al., "Base catalyzed degradations of rapamycin", *Tetrahedron Lett.,* 1993, 34(23), 3699–702.

Nicolaou, K.C. et al., "Total Synthesis of rapamycin", *J. Am. Chem. Soc.,* 1993, 115(10), 4419–20.

Hayward, C.M. et al., "Total Synthesis of rapamycin via a novel titanium–mediated aldol macrocyclization reaction", *J. Am. Chem. Soc.,* 1993, 115(20), 9345–6.

Yohannes, Daniel et al., "Degradation of rapamycin: synthesis of a rapamycin–derived fragment containing the tricarbonyl and triene sectors", *Tetrahderon Lett.,* 1993, 34(13), 2075–8.

Luengo, J. et al., "Studies on the chemistry of rapamycin: novel transformation under Lewis–acid catalysis", *Tetrahedron Lett.,* 1993, 34(6), 991–4.

Yohannes, Daniel et al., "Degradation of rapamycin: retrieval of major intact subunits", *Tetrahedron Lett.,* 1992, 33(49), 7469–72.

Goulet, Mark T. et al., "Degradative studies on the tricarbonyl containing macrolide rapamycin", *Tetrahedron Lett.,* 1991, 32(45), 6454.

Goulet, Mark T. et al., "Construction of the FK–506 analog from rapamycin–derived materials", *Tetrahedron Lett.,* 1991, 32(36), 4627–30.

Rao, A.V. Rama et al., "Studies directed towards the synthesis of immunosuppressive agent FK–506 synthesis of the entire bottom half", *Tetrahedron Lett.,* 1991, 32(9), 1251–4.

Fisher, Matthew, et al., "One the remarkable propensity for carbon–carbon bond cleavage reaction in the C(8)–C(10) region of FK–506", *J. Org. Chem.,* 1991, 56(8), 2900–7.

Linde, Robert G. et al., "Straightforward synthesis of 1,2, 3–tricarbonyl systems", *J. Org. Chem.,* 1991, 56(7), 2534–8.

Hayward, C.M. et al., "An application of the Suarez reaction to the regiospecific synthesis of the C28–C42 segment of rapamycin", 3989–92.

Hovarth, R. et al., "An application of the Evans–Prasad 1,3–Syn diol synthesis to a stereospecific synthesis of the $C_{10}$–$C_{27}$ segment of rapamycin", *Tetrahedron Lett.,* 1993, 34(25), 3993–3996.

Whitesell, J.K. et al., "Asymmetric Induction. Reduction, Nucleophilic Addition to, Ene Reactions of Chiral α–Ketoesters", *J. Chem. Soc., Chem. Commun.,* 1983, 802.

Ando, Takao et al., "Formation of Crossed Phenzine from the Reaction between Tetra–p–anisyl– and tetra–p–tolyl–hydrazines in Liquid Sulphur Dioxide", *Chem. Comm., S. Chem. Comm.,* 1975, 989.

Kino, Toru et al., "FK–506, a novel immunosuppressant isolated from A Streptomyces", *J. of Antibiotics,* 1987, 40(9), 1249–55.

Waldmann, Herbert, "Proline benzyl ester as chiral auxiliary in Barbier–type reactions in aqueous solution", *Synlett,* 1990, 10, 627–8.

Hauske, James R. et al., "Design and Synthesis of Novel FKBP Inhibitors", *J. Med. Chem.,* 1992, 35, 4284–96.

Holt, Dennis A. et al., "Structure–Activity Studies of Non-macrocyclic Rapamycin Derivatives", *Bioorganic & Medical Chemistry Letters,* 1993, vol. 3, No. 10, 1977–80.

Yamashita, Dennis S. et al., "Design Synthesis and Evaluation of Dual Domain FKBP Ligands", *Bioorg. Med. Chem. Lett.,* 1994, 4(2), 325–8.

Teague, Simon J. et al., "Synthesis and Study of a Non–Macrocyclic FK506 Derivative", *Bioorg. Med. Chem. Lett.,* 1994, 4(13), 1581–4.

Luengo, Juan I. et al., "Synthesis and Structure–Activity Relationships of Macrocyclic FKBP Ligands", *Bioorg. Med. Chem. Lett.,* 1994, 4(2), 321–4.

Holt, Dennis A. et al., "Structure–Activity Studies of Synthetic FKBP Ligands as Peptidyl–Prolyl Isomerase Inhibitors", *Bioorg. Med. Chem. Lett.,* 1994, 4(2), 315–20.

Teague, Simon J. et al., "The Affinity of the Excised Binding Domain of FK–506 for the Immunophilin FKBP12", *Bioorg. Med. Chem. Lett.,* 1993, 3(10), 1947–50.

Caffrey, Moya V. et al., "Synthesis and Evaluation of Dual Domain Macrocyclic FKBP12 Ligands", *Bioorg. Med. Chem. Lett.,* 4(21), 2507–10.

Birkenshaw, Timothy N. et al., "Synthetic FKBP12 Ligands. Design and Synthesis of Pyranose Replacements", *Bioorg. Med. Chem. Lett.,* 1994, 4(21), 2501–6.

Holt, Dennis A. et al., "Design, Synthesis, and Kinetic Evaluation of High–Affinity FKBP Ligands and the X–ray Crystal Structures of Their Complexes with FKBP12", *J. Am. Chem. Soc.,* 1993, 115, 9925–38.

Wang, Gary T. et al., "Synthesis and FKBP Binding of Small Molecule Mimics of the Tricarbonyl Region of FK506", *Bioorg. Med. Chem. Lett.,* 1994, 4(9), 1161–6.

Snyder, Solomon H. et al., "Immunophilins and the Nervous System", *Nature Medicine,* 1995, 1(1), 32–7.

Stocks, Michael J. et al., "The Contribution to Binding of the Pyranoside Substituents in the Excised Binding Domain of FK–506", *Bioorg. Med. Chem. Lett.,* 1994, 4(12), 1457–60.

Dumont, Francis J. et al., "The Immunosuppressive and Toxic Effects of FK–506 are Mechanistically Related: Pharmacology of a Novel Antagonist of FK–506 and Rapamycin", *J. Exp. Med.,* 1992, 176, 751–60.

Schreiber, Stuart L., "Chemistry and Biology of the Immunophilins and Their Immunosuppressive Ligands", *Science,* 1991, 251, 282–7.

* cited by examiner

Neurite Outgrowth in Sensory Neuronal Cultures

1 pM 10 pM 100 pM

Neurite Outgrowth in Sensory Neuronal Cultures 10 pM            100 pM            10 nM

HETEROCYCLIC ESTERS AND AMIDES

This is a divisional application of U.S. patent application Ser. No. 09/027,622, filed Feb. 23, 1998, which is a divisional application of U.S. patent application Ser. No. 08/719,947, filed Sep. 25, 1996 now U.S. Pat. No. 5,801,187 granted Sep. 1, 1998.

BACKGROUND OF THE INVENTION

1. Field of Invention

This invention relates to neurotrophic low molecular weight, small molecule heterocyclic esters and amides having an affinity for FKBP-type immunophilins, and their use as inhibitors of the enzyme activity associated with immunophilin proteins, particularly peptidyl-prolyl isomerase, or rotamase, enzyme activity.

2. Description of Related Art

The term immunophilin refers to a number of proteins that serve as receptors for the principal immunosuppressant drugs, cyclosporin A (CsA), FK506 and rapamycin. Known classes of immunophilins are cyclophilins and FK506 binding proteins, or FKBPs. Cyclosporin A binds to cyclophilin A while FK506 and rapamycin bind to FKBP12. These immunophilin-drug complexes interface with various intracellular signal transduction systems, especially the immune and nervous systems.

Immunophilins are known to have peptidyl-prolyl isomerase (PPIase), or rotamase, enzyme activity. It has been determined that rotamase enzyme activity plays a role in the catalyzation of the interconversion of the cis and trans isomers of peptide and protein substrates for the immunophilin proteins.

Immunophilins were originally discovered and studied in the immune tissue. It was initially postulated by those skilled in the art that inhibition of the immunophilins' rotamase activity leads to inhibition of T-cell proliferation, thereby causing the immunosuppressive activity exhibited by immunosuppressant drugs, such as cyclosporin A, FK506 and rapamycin. Further study has shown that the inhibition of rotamase activity, in and of itself, does not result in immunosuppressive activity. Schreiber et al., *Science,* 1990, vol. 250, pp. 556–559. Instead, immunosuppression appears to stem from the formulation of a complex of immunosuppressant drugs and immunophilins. It has been shown that the immunophilin-drug complexes interact with ternary protein targets as their mode of action. Schreiber et al., *Cell,* 1991, vol. 66, pp. 807–815. In the case of FKBP-FK506 and cyclophilin-CsA, the immunophilin-drug complexes bind to the enzyme calcineurin and inhibit the T-cell receptor signalling which leads to T-cell proliferation. Similarly, the immunophilin-drug complex of FKBP-rapamycin interacts with the RAFT1/FRAP protein and inhibits the IL-2 receptor signalling.

Immunophilins have been found to be present at high concentrations in the central nervous system. Immunophilins are enriched 10–50 times more in the central nervous system than in the immune system. Within neural tissues, immunophilins appear to influence nitric oxide synthesis, neurotransmitter release and neuronal process extension.

It has been found that picomolar concentrations of an immunosuppressant such as FK506 and rapamycin stimulate neurite outgrowth in PC12 cells and sensory neurons, namely dorsal root ganglion cells (DRGs). Lyons et al., *Proc. of Natl. Acad. Sci.,* 1994, vol. 91, pp. 3191–3195. In whole animal experiments, FK506 has been shown to stimulate nerve regeneration following facial nerve injury.

Surprisingly, it has been found that certain compounds with a high affinity for FKBPs are potent rotamase inhibitors and exhibit excellent neurotrophic effects. Furthermore, these rotamase inhibitors are devoid of immunosuppressive activity. These findings suggest the use of rotamase inhibitors in treating various peripheral neuropathies and enhancing neuronal regrowth in the central nervous system (CNS). Studies have demonstrated that neurodegenerative disorders such as Alzheimer's disease, Parkinson's disease, and amyotrophic lateral sclerosis (ALS) may occur due to the loss, or decreased availability, of a neurotrophic substance specific for a particular population of neurons affected in the disorder.

Several neurotrophic factors affecting specific neuronal populations in the central nervous system have been identified. For example, it has been hypothesized that Alzheimer's disease results from a decrease or loss of nerve growth factor (NGF). It has thus been proposed to treat SDAT patients with exogenous nerve growth factor or other neurotrophic proteins, such as brain derived growth factor, glial derived growth factor, ciliary neurotrophic factor and neurotropin-3, to increase the survival of degenerating neuronal populations.

Clinical application of these proteins in various neurological disease states is hampered by difficulties in the delivery and bioavailability of large proteins to nervous system targets. By contrast, immunosuppressant drugs with neurotrophic activity are relatively small and display excellent bioavailability and specificity. However, when administered chronically, immunosuppressant drugs exhibit a number of potentially serious side effects including nephrotoxicity, such as impairment of glomerular filtration and irreversible interstitial fibrosis (Kopp et al., *J. Am. Soc. Nephrol.,* 1991, 1:162); neurological deficits, such as involuntary tremors, or non-specific cerebral angina, such as non-localized headaches (De Groen et al., *N. Engl. J. Med.,* 1987, 317:861); and vascular hypertension with complications resulting therefrom (Kahan et al., *N. Engl. J. Med.,* 1989, 321:1725).

In order to prevent the side effects associated with use of the immunosuppressant compounds, the present invention provides non-immunosuppressive compounds containing small molecule FKBP rotamase inhibitors for enhancing neurite outgrowth, and promoting neuronal growth and regeneration in various neuropathological situations where neuronal repair can be facilitated, including: peripheral nerve damage caused by physical injury or disease state such as diabetes; physical damage to the central nervous system (spinal cord and brain); brain damage associated with stroke; and neurological disorders relating to neurodegeneration, such as Parkinson's disease, SDAT (Alzheimer's disease), and amyotrophic lateral sclerosis.

SUMMARY OF THE INVENTION

The present invention relates to neurotrophic low molecular weight, small molecule compounds having an affinity for FKBP-type immunophilins. Once bound to these proteins, the neurotrophic compounds are potent inhibitors of the enzyme activity associated with immunophilin proteins, particularly peptidyl-prolyl isomerase, or rotamase, enzyme activity. A key feature of the compounds of the present invention is that they do not exert any significant immunosuppressive activity in addition to their neurotrophic activity.

Specifically, the present invention relates to a compound of formula I:

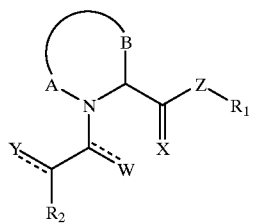

or a pharmaceutically acceptable salt thereof, wherein:

A and B, together with the nitrogen and carbon atoms to which they are respectively attached, form a 5–7 membered saturated or unsaturated heterocyclic ring containing, in addition to the nitrogen atom, at least one additional O, S, SO, $SO_2$, NH or $NR_1$ heteroatom in any chemically stable oxidation state;

X is O or S;

Z is O, NH or $NR_1$;

W and Y are independently O, S, $CH_2$ or $H_2$;

$R_1$ is $C_1$–$C_6$ straight or branched chain alkyl or alkenyl, which is substituted in one or more position(s) with $(Ar_1)_n$, $(Ar_1)_n$ connected by a $C_1$–$C_6$ straight or branched chain alkyl or alkenyl, $C_3$–$C_8$ cycloalkyl, $C_3$–$C_8$ cycloalkyl connected by a $C_1$–$C_6$ straight or branched chain alkyl or alkenyl, $Ar_2$, or a combination thereof;

n is 1 or 2;

$R_2$ is either $C_1$–$C_9$ straight or branched chain alkyl or alkenyl, $C_3$–$C_8$ cycloalkyl, $C_5$–$C_7$ cycloalkenyl, or $Ar_1$, wherein said alkyl, alkenyl, cycloalkyl or cycloalkenyl is either unsubstituted or substituted in one or more position(s) with $C_1$–$C_4$ straight or branched chain alkyl or alkenyl, hydroxyl, or a combination thereof; and $Ar_1$ and $Ar_2$ are independently a mono-, bi- or tricyclic, carbo- or heterocyclic ring, wherein the ring is either unsubstituted or substituted in one to three position(s) with halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, amino, or a combination thereof; wherein the individual ring sizes are 5–6 members; and wherein the heterocyclic ring contains 1–6 heteroatom(s) selected from the group consisting of O, N, S, and a combination thereof.

A preferred embodiment of this invention is a compound of formula II:

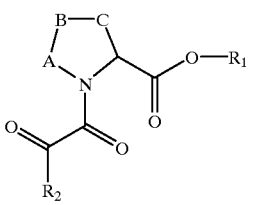

or a pharmaceutically acceptable salt thereof, wherein:

A, B and C are independently $CH_2$, O, S, SO, $SO_2$, NH or $NR_1$;

$R_1$ is $C_1$–$C_5$ straight or branched chain alkyl or alkenyl, which is substituted in one or more position(s) with $(Ar_1)_n$, $(Ar_1)_n$ connected by a $C_1$–$C_6$ straight or branched chain alkyl or alkenyl, or a combination thereof;

n is 1 or 2;

$R_2$ is either $C_1$–$C_9$ straight or branched chain alkyl or alkenyl, $C_3$–$C_8$ cycloalkyl, $C_5$–$C_7$ cycloalkenyl, or $Ar_1$; and $Ar_1$ is a mono-, bi- or tricyclic, carbo- or heterocyclic ring, wherein the ring is either unsubstituted or substituted in one to three position(s) with halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, amino, or a combination thereof; wherein the individual ring sizes are 5–6 members; and wherein the heterocyclic ring contains 1–6 heteroatom(s) selected from the group consisting of O, N, S, and a combination thereof.

Another preferred embodiment is a compound of formula III:

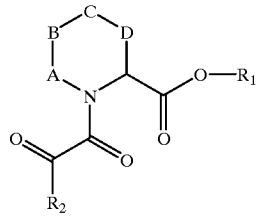

or a pharmaceutically acceptable salt thereof, wherein:

A, B, C and D are independently $CH_2$, O, S, SO, $SO_2$, NH or NR $R_1$;

$R_1$ is $C_1$–$C_5$ straight or branched chain alkyl or alkenyl, which is substituted in one or more position(s) with $(Ar_1)_n$, $(Ar_1)_n$ connected by a $C_1$–$C_6$ straight or branched chain alkyl or alkenyl, or a combination thereof;

n is 1 or 2;

$R_2$ is either $C_1$–$C_9$ straight or branched chain alkyl or alkenyl, $C_3$–$C_8$ cycloalkyl, $C_5$–$C_7$ cycloalkenyl, or $Ar_1$; and $Ar_1$ is a mono-, bi- or tricyclic, carbo- or heterocyclic ring, wherein the ring is either unsubstituted or substituted in one to three position(s) with halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, amino, or a combination thereof; wherein the individual ring sizes are 5–6 members; and wherein the heterocyclic ring contains 1–6 heteroatom(s) selected from the group consisting of O, N, S, and a combination thereof.

The present invention also relates to a pharmaceutical composition comprising a neurotrophically effective amount of the compound of formula I, II or III, and a pharmaceutically acceptable carrier.

The present invention further relates to a method of effecting a neuronal activity in an animal, comprising:

administering to the animal a neurotrophically effective amount of the compound of formula I, II or III.

DETAILED DESCRIPTION OF THE INVENTION

Definitions

Figure 1A:
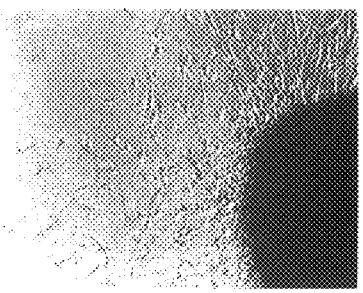
FIG. 1(A) is a representative photomicrograph of compound 1 (1 pM) promoting neurite outgrowth in sensory neurons.

"Alkyl" means a branched or unbranched saturated hydrocarbon chain containing 1 to 6 carbon atoms, such as methyl, ethyl, propyl, iso-propyl, butyl, iso-butyl, tert-butyl, n-pentyl, n-hexyl, and the like, unless otherwise indicated.

"Alkoxy" means the group —OR wherein R is alkyl as herein defined. Preferably, R is a branched or unbranched saturated hydrocarbon chain containing 1 to 3 carbon atoms.

"Halo" means fluoro, chloro, bromo, or iodo, unless otherwise indicated.

"Phenyl" includes all possible isomeric phenyl radicals, optionally monosubstituted or multi-substituted with substituents selected from the group consisting of alkyl, alkoxy, hydroxy, halo, and haloalkyl.

The term "pharmaceutically acceptable salt" refers to salts of the subject compounds which posses the desired pharmacological activity and which are neither biologically nor otherwise undesirable. The salts can be formed with inorganic acids such as acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate heptanoate, hexanoate, hydrochloride hydrobromide, hydroiodide, 2-hydroxyethanesulfonate, lactate, maleate, methanesulfonate, 2-naphthalenesulfonate, nicotinate, oxalate, thiocyanate, tosylate and undecanoate. Base salts include ammonium salts, alkali metal salts such as sodium and potassium salts, alkaline earth metal salts such as calcium and magnesium salts, salt with organic bases such as dicyclohexylamine salts, N-methyl-D-glucamine, and salts with amino acids such as arginine, lysine, and so forth. Also, the basic nitrogen-containing groups can be quarternized with such agents as lower alkyl halides, such as methyl, ethyl, propyl, and butyl chloride, bromides and iodides; dialkyl sulfates like dimethyl, diethyl, dibutyl and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

The compounds of this invention possess asymmetric centers and thus can be produced as mixtures of stereoisomers or as individual stereoisomers. The individual stereoisomers may be obtained by using an optically active starting material, by resolving a racemic or non-racemic mixture of an intermediate at some appropriate stage of the synthesis, or by resolution of the compound of formula (I). It is understood that the individual stereoisomers as well as mixtures (racemic and non-racemic) of stereoisomers are encompassed by the scope of the present invention. The compounds of this invention possess at least one asymmetric centers and thus can be produced as mixtures of stereoisomers or as individual R- and S-stereoisomers. The individual enantiomers may be obtained by resolving a racemic or non-racemic mixture of an intermediate at some appropriate stage of the synthesis. It is understood that the individual R- and S- stereoisomers as well as mixtures of stereoisomers are encompassed by this invention. The S-stereoisomer is most preferred due to its greater activity.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other.

"Diastereoisomers" are stereoisomers which are not mirror images of each other.

"Racemic mixture" means a mixture containing equal parts of individual enantiomers. "Non-racemic mixture" is a mixture containing unequal parts of individual enantiomers or stereoisomers.

The term "treatment" as used herein covers any treatment of a disease and/or condition in an animal, particularly a human, and includes:

(i) preventing a disease and/or condition from occurring in a subject which may be predisposed to the disease and/or condition but has not yet been diagnosed as having it;

(ii) inhibiting the disease and/or condition, i.e., arresting its development; or (iii) relieving the disease and/or condition, i.e., causing regression of the disease and/or condition.

The system used in naming the compounds of the present invention is shown below, using a compound of formula II as an example.

A compound of formula II wherein A is $CH_2$, B is S, C is $CH_2$, $R_1$ is 3-phenylpropyl and $R_2$ is 3,3-dimethylpentyl, is named 3-phenyl-1-propyl(2S)-1-(3,3-dimethyl-1,2-dioxopentyl)-2-(4-thiazolidine)carboxylate.

Compounds of the Invention

The neurotrophic low molecular weight, small molecule FKBP inhibitor compounds of this invention have an affinity for FKBP-type immunophilins, such as FKBP12. When the neurotrophic compounds of this invention are bound to an FKBP-type immunophilin, they have been found to inhibit the prolyl-peptidyl cis-trans isomerase activity, or rotamase, activity of the binding protein and unexpectedly stimulate neurite growth.

Formula I

In particular, this invention relates to a compound of formula I:

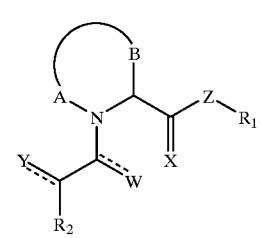

I or a pharmaceutically acceptable salt thereof, wherein:

A and B, together with the nitrogen and carbon atoms to which they are respectively attached, form a 5–7 membered saturated or unsaturated heterocyclic ring containing, in addition to the nitrogen atom, at least one additional O, S, SO, $SO_2$, NH or $NR_1$ heteroatom in any chemically stable oxidation state;

X is O or S;

Z is O, NH or $NR_1$;

W and Y are independently O, S, $CH_2$ or $H_2$;

$R_1$ is $C_1$–$C_6$ straight or branched chain alkyl or alkenyl, which is substituted in one or more position(s) with $(Ar_1)_n$, $(Ar_1)_n$ connected by a $C_1$–$C_6$ straight or branched chain alkyl or alkenyl, $C_3$–$C_8$ cycloalkyl, $C_3$–$C_8$ cycloalkyl connected by a $C_1$–$C_6$ straight or branched chain alkyl or alkenyl, $Ar_2$, or a combination thereof;

n is 1 or 2;

$R_2$ is either $C_1$–$C_9$ straight or branched chain alkyl or alkenyl, $C_3$–$C_8$ cycloalkyl, $C_5$–$C_7$ cycloalkenyl, or $Ar_1$, wherein said alkyl, alkenyl, cycloalkyl or cycloalkenyl is either unsubstituted or substituted in one or more position(s) with $C_1$–$C_4$ straight or branched chain alkyl or alkenyl, hydroxyl, or a combination thereof; and $Ar_1$ and $Ar_2$ are independently a mono-, bi- or tricyclic, carbo- or heterocyclic ring, wherein the ring is either unsubstituted or substituted in one to three position(s) with halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, amino, or a combination thereof; wherein the individual ring sizes are 5–6 members; and wherein the heterocyclic ring contains 1–6 heteroatom(s) selected from the group consisting of O, N, S, and a combination thereof.

The mono- and bicyclic, carbo- and heterocyclic rings include without limitation naphthyl, indolyl, furyl, thiazolyl, thienyl, pyridyl, quinolinyl, isoquinolinyl, fluorenyl and phenyl.

Formula II

A preferred embodiment of this invention is a compound of formula II:

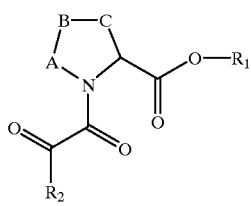

II or a pharmaceutically acceptable salt thereof, wherein:

A, B and C are independently $CH_2$, O, S, SO, $SO_2$, NH or $NR_1$;

$R_1$ is $C_1$–$C_5$ straight or branched chain alkyl or alkenyl, which is substituted in one or more positions) with $(Ar_1)_n$, $(Ar_1)_n$ connected by a $C_1$–$C_6$ straight or branched chain alkyl or alkenyl, or a combination thereof;

n is 1 or 2;

$R_2$ is either $C_1$–$C_9$ straight or branched chain alkyl or alkenyl, $C_3$–$C_8$ cycloalkyl, $C_5$–$C_7$ cycloalkenyl, or $Ar_1$; and $Ar_1$ is a mono-, bi- or tricyclic, carbo- or heterocyclic ring, wherein the ring is either unsubstituted or substituted in one to three position(s) with halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, amino, or a combination thereof; wherein the individual ring sizes are 5–6 members; and wherein the heterocyclic ring contains 1–6 heteroatom(s) selected from the group consisting of O, N, S, and a combination thereof.

In a particularly preferred embodiment of formula II compounds:

A is $CH_2$;

B is $CH_2$ or S;

C is $CH_2$ or NH;

$R_1$ is selected from the group consisting of 3-phenylpropyl and 3-(3-pyridyl)propyl; and $R_2$ is selected from the group consisting of 3,3-dimethylpentyl, cyclohexyl, and tert-butyl.

Specific exemplifications of this embodiment are presented in TABLE I.

TABLE I

| No. | A | B | C | $R_1$ | $R_2$ |
|---|---|---|---|---|---|
| 1 | $CH_2$ | S | $CH_2$ | 3-phenylpropyl | 3,3-dimethylpentyl |
| 2 | $CH_2$ | S | $CH_2$ | 3-(3-pyridyl)propyl | 3,3-dimethylpentyl |
| 3 | $CH_2$ | S | $CH_2$ | 3-phenylpropyl | cyclohexyl |
| 4 | $CH_2$ | S | $CH_2$ | 3-phenylpropyl | tert-butyl |
| 5 | $CH_2$ | $CH_2$ | NH | 3-phenylpropyl | 3,3-dimethylpentyl |
| 6 | $CH_2$ | $CH_2$ | NH | 3-phenylpropyl | cyclohexyl |
| 7 | $CH_2$ | $CH_2$ | NH | 3-phenylpropyl | tert-butyl |

Formula III

Another preferred embodiment of this invention is a compound of formula III:

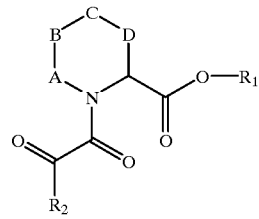

III or a pharmaceutically acceptable salt thereof, wherein:

A, B, C and D are independently $CH_2$, O, S, SO, $SO_2$, NH or $NR_1$;

$R_1$ is $C_1$–$C_5$ straight or branched chain alkyl or alkenyl, which is substituted in one or more position(s) with $(Ar_1)_n$, $(Ar_1)_n$ connected by a $C_1$–$C_6$ straight or branched chain alkyl or alkenyl, or a combination thereof;

n is 1 or 2;

$R_2$ is either $C_1$–$C_9$ straight or branched chain alkyl or alkenyl, $C_3$–$C_8$ cycloalkyl, $C_5$–$C_7$ cycloalkenyl, or $Ar_1$; and $Ar_1$ is a mono-, bi- or tricyclic, carbo- or heterocyclic ring, wherein the ring is either unsubstituted or substituted in one to three position(s) with halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, amino, or a combination thereof; wherein the individual ring sizes are 5–6 members; and wherein the heterocyclic ring contains 1–6 heteroatom(s) selected from the group consisting of O, N, S, and a combination thereof.

In a particularly preferred embodiment of formula III compounds:

A is $CH_2$;

B is $CH_2$;

C is S, O or NH;

D is $CH_2$;

$R_1$ is selected from the group consisting of 3-phenylpropyl and (3,4,5-trimethoxy)phenylpropyl; and $R_2$ is selected from the group consisting of 3,3-dimethylpentyl, cyclohexyl, 3-3-dimethylpropyl, phenyl, and 3,4,5-trimethoxyphenyl.

Specific exemplifications of this embodiment are presented in TABLE II.

TABLE II

| No. | A | B | C | D | R₁ | R₂ |
|---|---|---|---|---|---|---|
| 8 | $CH_2$ | $CH_2$ | S | $CH_2$ | 3-phenylpropyl | 3,3-dimethylpentyl |
| 9 | $CH_2$ | $CH_2$ | O | $CH_2$ | 3-phenylpropyl | 3,3-dimethylpentyl |
| 10 | $CH_2$ | $CH_2$ | S | $CH_2$ | 3-phenylpropyl | cyclohexyl |
| 11 | $CH_2$ | $CH_2$ | O | $CH_2$ | 3-phenylpropyl | cyclohexyl |
| 12 | $CH_2$ | $CH_2$ | S | $CH_2$ | 3-phenylpropyl | phenyl |
| 13 | $CH_2$ | $CH_2$ | O | $CH_2$ | 3-phenylpropyl | phenyl |
| 14 | $CH_2$ | $CH_2$ | NH | $CH_2$ | 3-phenylpropyl | 3,3-dimethylpentyl |
| 15 | $CH_2$ | $CH_2$ | NH | $CH_2$ | 3-phenylpropyl | phenyl |

The compounds of the present invention exist as stereoisomeric forms, either enantiomers or diastereoisomers. Included within the scope of the invention are the enantiomers, the racemic form, and diastereoisomeric mixtures. Enantiomers and diastereoisomers can be separated by methods known to those skilled in the art.

Methods of Using the Compounds of the Invention

The compounds of the present invention have an affinity for the FK506 binding protein, particularly FKBP12, which is present in the brain. When the inventive compounds bind to FKBP in the brain, they exhibit excellent neurotrophic activity. This activity is useful in the stimulation of damaged neurons, the promotion of neuronal regeneration, the prevention of neurodegeneration, and the treatment of several neurological disorders known to be associated with neuronal degeneration and peripheral neuropathies.

For the foregoing reasons, the present invention further relates to a method of effecting a neuronal activity in an animal, comprising:

administering to the animal a neurotrophically effective amount of a compound of formula I, II or III.

In a preferred embodiment, the neuronal activity is selected from the group consisting of stimulation of damaged neurons, promotion of neuronal regeneration, prevention of neurodegeneration and treatment of neurological disorder.

The neurological disorders that may be treated include but are not limited to: trigeminal neuralgia; glossopharyngeal neuralgia; Bell's Palsy; myasthenia gravis; muscular dystrophy; amyotrophic lateral sclerosis; progressive muscular atrophy; progressive bulbar inherited muscular atrophy; herniated; ruptured or prolapsed invertabrae disk syndromes; cervical spondylosis; plexus disorders; thoracic outlet destruction syndromes; peripheral neuropathic such as those caused by lead, dapsone, ticks, porphyria, or Gullain-Barré syndrome; Alzheimer's disease; and Parkinson's disease.

The compounds of the present invention are particularly useful for treating a neurological disorder selected from the group consisting of: peripheral neuropathy caused by physical injury or disease state, physical damage to the brain, physical damage to the spinal cord, stroke associated with brain damage, and neurological disorder relating to neurodegeneration. Examples of neurological disorders relating to neurodegeneration are Alzheimer's Disease, Parkinson's Disease, and amyotrophic lateral sclerosis.

For these purposes the compounds of the present invention may be administered orally, parenterally, by inhalation spray, topically, rectally, nasally, buccally, vaginally or via an implanted reservoir in dosage formulations containing conventional non-toxic pharmaceutically-acceptable carriers, adjuvants and vehicles. The term parenteral as used herein includes subcutaneous, intravenous, intramuscular, intraperitoneally, intrathecally, intraventricularly, intrasternal and intracranial injection or infusion techniques.

To be effective therapeutically as central nervous system targets, the compounds of the present invention should readily penetrate the blood-brain barrier when peripherally administered. Compounds which cannot penetrate the blood-brain barrier can be effectively administered by an intraventricular route.

The compounds of the present invention may be administered in the form of sterile injectable preparations, for example, as sterile injectable aqueous or oleaginous suspensions. These suspensions may be formulated according to techniques known in the art using suitable dispersing or wetting agents and suspending agents. The sterile injectable preparations may also be sterile injectable solutions or suspensions in non-toxic parenterally-acceptable diluents or solvents, for example, as solutions in 1,3-butanediol. Among the acceptable vehicles and solvents that may be employed are water, Ringer's solution and isotonic sodium chloride solution. in addition, sterile, fixed oils are conventionally employed as solvents or suspending mediums. For this purpose, any bland fixed oil may be employed including synthetic mono- or di-glycerides. Fatty acids such as oleic acid and its glyceride derivatives, including olive oil and castor oil, especially in their polyoxyethylated versions, are useful in the preparation of injectables. These oil solutions or suspensions may also contain long-chain alcohol diluents or dispersants.

The compounds may be administered orally in the form of capsules, tablets, aqueous suspensions or solutions. Tablets may contain carriers such as lactose and corn starch, and/or lubricating agents such as magnesium stearate. Capsules may contain diluents including lactose and dried corn starch. Aqueous suspensions may contain emulsifying and suspending agents combined with the active ingredient. The oral dosage forms may further contain sweetening and/or flavoring and/or coloring agents.

The compounds of this invention may also be administered rectally in the form of suppositories. These compositions can be prepared by mixing the drug with a suitable non-irritating excipient which is solid at room temperature, but liquid at rectal temperature and, therefore, will melt in the rectum to release the drug. Such materials include cocoa butter, beeswax and polyethylene glycols.

The compounds of this invention may also be administered topically, especially when the conditions addressed for treatment involve areas or organs readily accessible by topical application, including neurological disorders of the eye, the skin, or the lower intestinal tract. Suitable topical formulations are readily prepared for each of these areas.

For topical application to the eye, or ophthalmic use, the compounds can be formulated as micronized suspensions in isotonic, pH adjusted sterile saline, or, preferably, as solutions in isotonic, pH adjusted sterile saline, either with or without a preservative such as benzylalkonium chloride. Alternatively for the ophthalmic uses the compounds may be formulated in an ointment such as petrolatum.

For topical application to the skin, the compounds can be formulated in a suitable ointment containing the compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, the compounds can be formulated in a suitable lotion or cream containing the active compound suspended or dissolved in, for example, a mixture of one or more of the following: mineral oil, sorbitan monostearate, polysorbate 60, cetyl esters wax, cetearyl alcohol, 2-octyldodecanol, benzyl alcohol and water.

Topical application for the lower intestinal tract an be effected in a rectal suppository formulation (see above) or in a suitable enema formulation.

Dosage levels on the order of about 0.1 mg to about 10,000 mg of the active ingredient compound are useful in the treatment of the above conditions, with preferred levels of about 0.1 mg to about 1,000 mg. The amount of active ingredient that may be combined with the carrier materials to produce a single dosage form will vary depending upon the host treated and the particular mode of administration.

It is understood, however, that a specific dose level for any particular patient will depend upon a variety of factors including the activity of the specific compound employed, the age, body weight, general health, sex, diet, time of administration, rate of excretion, drug combination, and the severity of the particular disease being treated and form of administration.

The compounds can be administered with other neurotrophic agents such as neurotrophic growth factor (NGF), glial derived growth factor, brain derived growth factor, ciliary neurotrophic factor, and neurotropin-3. The dosage level of other neurotrophic drugs will depend upon the factors previously stated and the neurotrophic effectiveness of the drug combination.

Pharmaceutical Compositions of the Invention

The present invention also relates to a pharmaceutical composition comprising:

(i) a neurotrophically effective amount of the compound of formula I, II or III, and (ii) a pharmaceutically acceptable carrier.

The above discussion relating to the utility and administration of the compounds of the present invention also applies to the pharmaceutical compositions of the present invention.

EXAMPLES

The following examples are illustrative of the present invention and are not intended to be limitations thereon. Unless otherwise specified, all percentages are based on 100% by weight of the final compound.

Example 1

Synthesis of 3-phenyl-1-propyl(2S)-1-(3,3-dimethyl-1,2-dioxopentyl)-2-(4-thiazolidine) carboxylate (1)

1-(1,2-dioxo-2-methoxyethyl)2-(4-thiazolidine)-carboxylate. A solution of L-thioproline (1.51 g; 11.34 mmol) in 40 mL of dry methylene chloride was cooled to 0° C. and treated with 3.3 mL (2.41 g; 23, 81 mmol) of triethylamine. After stirring this mixture for 30 minutes, a solution of methyl oxalyl chloride (1.81 g; 14.74 mmol) was added dropwise. The resulting mixture was stirred at 0° C. for 1.5 hours, filtered through Celite to remove solids, dried and concentrated. The crude material was purified on a silic gel column, eluting with 10% MeOH in methylene chloride, to obtain 2.0 g of the oxamate as an orange-yellow solid.

3-phenyl-1-propyl(2S)-1-(1,2-dioxo-2-methoxyethyl)2-(4-thiazolidine)carboxylate. 1-(1,2-dioxo-2-methoxyethyl) 2-(4-thiazolidine)carboxylate (500 mg; 2.25 mmol), 3-phenyl-1-propanol (465 mg; 3.42 mmol), dicyclohexyl- carbodiimide (750 mg; 3.65 mmol), 4-dimethylaminopyridine (95 mg; 0.75 mmol) and camphorsulfonic acid (175 mg; 0.75 mmol) in 30 mL of methylene chloride were stirred together overnight. The mixture was filtered through Celite to remove solids and chromatographed (25% ethyl acetate/hexane) to obtain 690 mg of material, $^1$H NMR (CDCl$_3$, 300 MHz): δ1.92–2.01 (m, 2H); 2.61–2.69 (m, 2H); 3.34 (m, 1H); 4.11–4.25 (m, 2H); 4.73 (m, 1H); 5.34 (m, 1H); 7.12 (m, 3H); 7.23 (m, 2H).

3-phenyl-1-propyl(2S)-1-(3,3-dimethyl-1,2-dioxopentyl)-2-(4-thiazolidine)carboxylate (1). A solution of 3-phenyl-1-propyl(2S)-1-(1,2-dioxo-2-methoxyethyl)2-(4-thiazolidine)carboxylate (670 mg; 1.98 mmol) in tetrahydrofuran (10 mL) was cooled to −78° C. and treated with 2.3 mL of a 1.0 M solution of 1,1-dimethylpropylmagnesium chloride in ether. After stirring the mixture for 3 hours, it was poured into saturated ammonium chloride, extracted into ethyl acetate, and the organic phase was washed with water, dried and concentrated. The crude material was purified on a silica gel column, eluting with 25% ethyl acetate in hexane, to obtain 380 mg of the compound of Example 1 as a yellow oil, $^1$H NMR (CDCl$_3$, 300 MHz): d 0.86 (t, 3H); 1.21 (s, 3H); 1.26 (s, 3H); 1.62–1.91 (m, 3H); 2.01 (m, 2H); 2.71 (m, 2H); 3.26–3.33 (m, 2H); 4.19 (m, 2H); 4.58 (m, 1H); 7.19 (m, 3H); 7.30 (m, 2H). Anal. Clcd. for $C_{20}H_{27}NO_4S$: C, 63.63; H, 7.23; N, 3.71. Found: C, 64.29; H, 7.39; N, 3.46.

Example 2

Synthesis of 3-(3-pyridyl)-1-propyl(2S)-1-(3,3-dimethyl-1,2-dioxopentyl)-2-(4-thiazolidine) carboxylate (2)

The compound of Example 2 was prepared according to the procedure of Example 1, using 3-(3-pyridyl)-1-propanol in the final step, to yield 3-(3-pyridyl)-1-propyl(2S)-1-(3,3-dimethyl-1,2-dioxopentyl)-2-(4-thiazolidine)carboxylate, $^1$H NMR (CDCl$_3$, 300 MHz): δ0.89 (t, 3H, J=7.3); 1.25 (s, 3H); 1.28 (s, 3H); 1.77 (q, 2H, J=7.3); 2.03 (tt, 2H, J=6.4, 7.5); 2.72 (t, 2H, J=7.5); 3.20 (dd, 1H, J=4.0, 11.8); 3.23 (dd, 1H, J=7.0, 11.8); 4.23 (t, 2H, J=6.4); 4.55 (d, 2H, J=8.9); 5.08 (dd, 1H, J=4.0, 7.0); 7.24 (m, 1H); 8.48 (m, 2H). Anal. Calcd. for $C_{19}H_{26}N_2O_4S$–0.5 $H_2O$: C, 58.89; H, 7.02; N, 7.23. Found: C, 58.83; H, 7.05; N, 7.19.

As discussed above, the compounds of the present invention have an affinity for the FK506 binding protein, particularly FKBP12. The inhibition of the prolyl peptidyl cis-trans isomerase activity of FKBP may be measured as an indicator of this affinity.

Ki Test Procedure

Inhibition of the peptidyl-prolyl isomerase (rotamase) activity of the inventive compounds can be evaluated by known methods described in the literature (Harding, et al., *Nature*, 1989, 341:758–760; Holt et al. *J. Am. Chem. Soc.*, 115:9923–9938). These values are obtained as apparent Ki's and are presented in Table III. The cis-trans isomerization of an alanine-proline bond in a model substrate, N-succinyl-Ala-Ala-Pro-Phe-p-nitroanilide, is monitored spectrophotometrically in a chymotrypsin-coupled assay, which releases para-nitroanilide from the trans form of the substrate. The inhibition of this reaction caused by the addition of different concentrations of inhibitor is determined, and the data is analyzed as a change in first-order rate constant as a function of inhibitor concentration to yield the apparent Ki values.

In a plastic cuvette are added 950 mL of ice cold assay buffer (25 mM HEPES, pH 7.8, 100 mM NaCl), 10 mL of FKBP (2.5 mM in 10 mM Tris-Cl pH 7.5, 100 mM NaCl, 1 mM dithiothreitol), 25 mL of chymotrypsin (50 mg/ml in 1 mM HCl) and 10 mL of test compound at various concentrations in dimethyl sulfoxide. The reaction is initiated by the addition of 5 mL of substrate (succinyl-Ala-Phe-Pro-Phe-para-nitroanilide, 5 mg/mL in 2.35 mM LiCl in trifluoroethanol).

The absorbance at 390 nm versus time is monitored for 90 seconds using a spectrophotometer and the rate constants are determined from the absorbance versus time data files.

The data for these experiments for representative compounds are presented in Table III under the column "Ki".

The neurotrophic effects of the compounds of the present invention can be demonstrated in cellular biological experiments in vitro, as described below.

Chick Dorsal Root Ganglion

Cultures and Neurite Outgrowth

Dorsal root ganglia were dissected from chick embryos of ten day gestation. Whole ganglion explants were cultured on thin layer Matrigel-coated 12 well plates with Liebovitz L15 plus high glucose media supplemented with 2 mM glutamine and 10% fetal calf serum, and also containing 10 $\mu$M cytosine $\beta$-D arabinofuranoside (Ara C) at 37° C. in an environment containing 5% $CO_2$. Twenty-four hours later, the DRGs were treated with various immunophilin ligands. Forty-eight hours after drug treatment, the ganglia were visualized under phase contrast or Hoffman Modulation contrast with a Zeiss Axiovert inverted microscope. Photomicrographs of the explants were made, and neurite outgrowth was quantitated. Neurites longer than the DRG diameter were counted as positive, with total number of neurites quantitated per each experimental condition. Three to four DRGs are cultured per well, and each treatment was performed in duplicate.

Figure 1B:
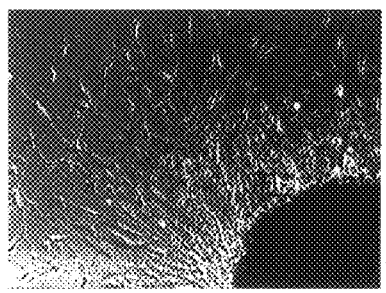
FIG. 1(B) is a representative photomicrograph of compound 1 (10 pM) promoting neurite outgrowth in sensory neurons.
Figure 1C:
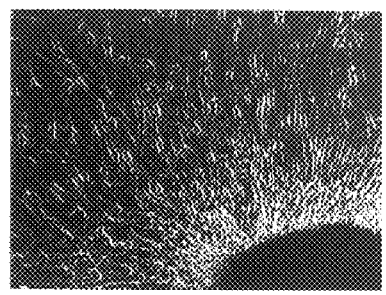
FIG. 1(C) is a representative photomicrograph of compound 1 (100 pM) promoting neurite outgrowth in sensory neurons.
Figure 2A:
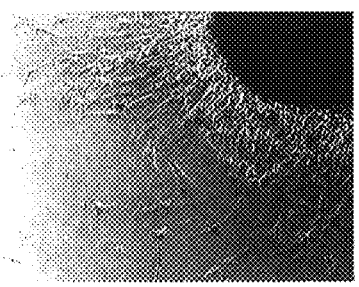
FIG. 2(A) is a representative photomicrograph of compound 2 (10 pM) promoting neurite outgrowth in sensory neurons.
Figure 2B:
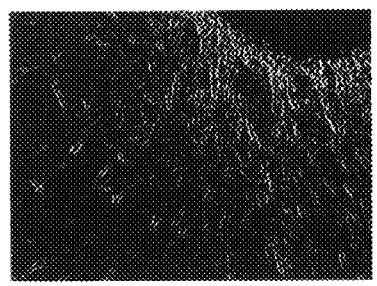
FIG. 2(B) is a representative photomicrograph of compound 2 (100 pM) promoting neurite outgrowth in sensory neurons.
Figure 2C:
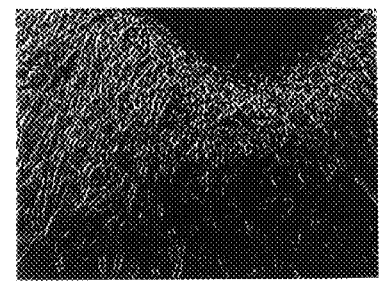
FIG. 2(C) is a representative photomicrograph of compound 2 (10 nM) promoting neurite outgrowth in sensory neurons.

The data for these experiments for representative compounds are presented in the "ED50" column of Table III. Representative photomicrographs of compounds 1 (1 pM, 10 pM, 100 pM) and 2 (10 pM, 100 pM, 10 nM) promoting neurite outgrowth in sensory neurons are shown in FIGS. 1(A–C) and 2(A–C), respectively.

TABLE III

| | In Vitro Test Results | |
|---|---|---|
| Compound | Ki, nM | ED50, nM |
| 1 | 215 | 0.031 |
| 2 | 638 | 2.0 |

All publications and patents identified above are hereby incorporated by reference.

The invention being thus described, it will be obvious that the same may be varied in many ways. Such variations are not to be regarded as a departure from the spirit and scope of the invention and all such modifications are intended to be included within the scope of the following claims.

What is claimed is:

1. The compound 1-(1,2-dioxo-2-methoxyethyl)2-(4-thiazolidine) carboxylic acid.

* * * * *